United States Patent [19]

Hölter et al.

[11] Patent Number: 5,066,466

[45] Date of Patent: * Nov. 19, 1991

[54] APPARATUS FOR INDICATING THE PRESENCE OF TOXIC SUBSTANCES IN AIR THAT IS SUPPLIED TO A PERSONNEL-OCCUPIED SPACE

[75] Inventors: Heinz Hölter, Beisenstrasse 39-41, 4390 Gladbeck; Heinrich Igelbüscher, Gladbeck; Heinrich Gresch, Dortmund-Wickede; Heribert Dewert, Gladbeck; Hanns Rump, Unna-Massen, all of Fed. Rep. of Germany

[73] Assignee: Heinz Hölter, Gladbeck, Fed. Rep. of Germany

[ * ] Notice: The portion of the term of this patent subsequent to Nov. 2, 2006 has been disclaimed.

[21] Appl. No.: 440,222

[22] Filed: Nov. 21, 1989

Related U.S. Application Data

[60] Division of Ser. No. 256,145, Oct. 5, 1988, Pat. No. 4,882,287, which is a continuation of Ser. No. 30,867, filed as a PCT EP86/00423 Jul. 18, 1986 published as WO87/00634 Jan. 29, 1987, abandoned.

[30] Foreign Application Priority Data

Jul. 19, 1985 [DE] Fed. Rep. of Germany ....... 3525774
Apr. 28, 1986 [DE] Fed. Rep. of Germany ....... 3614314
May 13, 1986 [DE] Fed. Rep. of Germany ....... 3616052

[51] Int. Cl.$^5$ .............................................. G01N 27/04
[52] U.S. Cl. .................................... 422/98; 422/83; 422/109; 340/632; 340/634
[58] Field of Search ............. 436/134, 137, 149; 422/83, 88, 90, 93, 98, 109; 73/23, 27 R, 31.02, 31.05, 31.06; 340/634, 632; 338/34; 357/25

[56] References Cited

U.S. PATENT DOCUMENTS

| | | | |
|---|---|---|---|
| 3,716,337 | 2/1973 | Jones | 422/93 |
| 3,765,842 | 10/1973 | Purt | 436/134 X |
| 3,851,520 | 12/1974 | Schluter et al. | 73/1 G |
| 3,926,561 | 12/1975 | Lucero | 422/83 |
| 4,002,223 | 12/1977 | Lamphere et al. | 73/27 R |
| 4,233,033 | 11/1980 | Eifler et al. | 422/90 |
| 4,352,087 | 9/1982 | Wittmaier | 340/634 |
| 4,498,330 | 2/1985 | Hosoya | 73/27 R |
| 4,519,237 | 5/1985 | Kubo | 73/23 |
| 4,533,520 | 8/1985 | Bossart et al. | 73/27 R |
| 4,644,333 | 2/1987 | Barendsz et al. | 340/634 |
| 4,730,479 | 3/1988 | Pyke et al. | 73/23 |
| 4,882,287 | 11/1989 | Hölter et al. | 436/806 X |

Primary Examiner—David L. Lacey
Assistant Examiner—Jeffrey R. Snay
Attorney, Agent, or Firm—Herbert Dubno

[57] ABSTRACT

The present invention relates to a device for indicating toxic substances in air that is supplied to accommodation used for personnel, preferably the cab of a motor vehicle, this having error compensation for humidity and temperature in one or a plurality of semiconductor gas sensors that are used, in which connection the sensor heating voltage is controlled to provide constant heating output and the sensor temperature pick up as well as the necessary amplifier (control stage) used to generate the temperature-varied heating voltage are arranged in a common housing, and that in the area of the sensors this housing is perforated. In order to permit compensation of the toxic substance, temperature, and humidity correlated output signals that are picked up, the present invention proposes that the characteristic curves of the sensor are reproduced in a voltage divider which, outside the sensor and jointly with the sensor forms a voltage divider for a common supply voltage, such that the influence factors compensate each other in equal proportional changes in value of both the sensor and of the outside wiring.

2 Claims, 3 Drawing Sheets

APPARATUS FOR INDICATING THE PRESENCE OF TOXIC SUBSTANCES IN AIR THAT IS SUPPLIED TO A PERSONNEL-OCCUPIED SPACE

This is a divisional of co-pending application Ser. No. 07/256,145 filed on Oct. 5, 1988, now U.S. Pat. No. 4,882,287 which is a continuation of application Ser. No. 30,867, filed as PCT EP 86/00423 on July 18, 1986, published as WO 87/00634 on Jan. 29, 1987, now abandoned.

CROSS REFERENCE TO RELATED APPLICATIONS

This application is a national phase application of PCT/EP86/00423 filed July 18, 1986 and based, in turn, on German national applications P35 25 774.1 filed July 19, 1985, P36 14 314.6 filed Apr. 28, 1986 and P 36 16 052.0 filed May 13, 1986.

FIELD OF THE INVENTION

The present invention relates to an apparatus for indicating the presence of toxic substances in air that is to be supplied to a cab, or the like, preferably the cab of a motor vehicle, used to accommodate personnel, this apparatus incorporating error compensation for humidity and temperature on one or a plurality of semiconductor gas sensors that are used, in which connection the sensor heating voltage is controlled to provide a constant heating output and the sensor temperature pick up as well as the necessary amplifier (control stage) used to generate the temperature-controlled heating voltage are arranged in a common housing, this housing being perforated in the region of the sensors.

BACKGROUND OF THE INVENTION

In order to remove toxic substances that are contained in air supplied for personnel it is first necessary to identify these substrates, in order that signals and/or manipulated variables can be generated so that filtering processes and/or ventilation systems can be either activated or shut down.

It has already been proposed that analytical devices be provided in order to detect toxic substances in the air; however, such devices are comparatively costly from the point of view of acquisition and operation, quite apart from the fact that they can only determine individual components of toxic substances.

Semiconductor-based sensors can also be used for this purpose, and generally speaking these fulfill the demand that they respond to the usual contaminants present in the air. However, with respect to their response sensitivity, the operating ranges of such sensors lie significantly above the concentration levels of many toxic substances which can be toxic to humans. Furthermore, semiconductor-based sensors are sensitive to temperature variations and different flow velocities of the air currents that are to be monitored. In addition, the response times of such sensors—particularly in the range of low concentrations—and their decontamination times are too high to permit them to be used, for example, to control filter systems and/or ventilation systems in a motor-vehicle cab.

OBJECT OF THE INVENTION

The present invention has as its object to provide an apparatus that is economical and requires little maintenance, that takes up little space, and with which the errors caused by humidity, temperature, or the like at the sensor can be compensated in a simple and precise manner and, at the same time, which avoids the disadvantages set out above.

SUMMARY OF THE INVENTION

In order to be able to compensate for the errors of the output signals that are picked up, which are correlated to toxic substance, temperature and humidity, the present invention provides that the characteristic curves of the sensors be reproduced in a voltage divider that outside of the sensor and together with the sensor forms a voltage divider for the common supply voltage, such that the limiting quantities compensate for each other in equal proportional changes in value both of the sensor and also in the outside wiring.

As a result, the output signal remains constant over the temperature range.

At the same time the sensor heating output also changes as a function of temperature.

At low temperatures the heating voltage, and thus the output, is increased, while the heating voltage is decreased at higher temperature.

In a preferred embodiment the heating voltage at 20° C. is 5 volts.

It is characteristic for $SnO_2$ detectors that the dependency on absolute air humidity is to a very great extent connected with the presence of carbon monoxide.

The sensitivity of the sensor to carbon monoxide is almost constant at varying heating output in a small range between approximately 4.8 and 5.2 volts, whereas the sensitivity relative to other gases falls off with increasing heating output.

The temperature-dependent modulation of the heating voltage and the calculation of the resistance network in the measuring branch is so dimensioned that the starting values with complex signals, as are present in road traffic exhaust gas, and which always contain both carbon monoxide and other compounds, repress the effect of humidity by the combination of heating modulation and the voltage divider network, because absolute humidity is coupled to a very great extent to air temperature, the temperature flow varies the heating voltage and thus the sensitivity to all gases apart from carbon monoxide, and the voltage divider in the measuring branch takes into account this additional change in addition to pure temperature sensitivity.

At the smaller concentrations of toxic substance present in road traffic the electrical components used to control fresh air flaps and/or filter apparatuses that are associated with the sensors must have very high amplification, in order that suitable switching signals can be generated although, of necessity, all the undersirable secondary effects will also be amplified.

In the case of toxic substances found in road traffic, these are, for the most part, gases with other specific characteristics than the component elements of non-polluted air.

By using suitable plastic foils that are of a specific structure, uncontaminating components of the air can, preferably, diffuse through these better, whereas with other foils practically all gases can pass unhindered through the foil.

Proceeding from this concept, the present invention thus provides that the sensors that are sensitive to the toxic substance be so installed they are acted upon by a flow of gas in which the concentration of toxic substances in the remaining gas flow has been increased by the previous removal of uncontaminating gas molecules by diffusion.

By this means it is possible to ensure that the semiconductor gas sensors that are used operate in higher concentrations of toxic substance and the effects of humidity, changing temperatures, air velocity, are so small that they can be disregarded.

It is known that semiconductor sensors register the presence of toxic substances, but cannot pick these up selectively.

In order to create a selective measurement process using semiconductor sensors, the present invention provides that two sensors that do not operate selectively be incorporated in series in the gas flow that is to be measured, and that a selective toxic substance precipitation and separation be effected between these two sensors.

This can be done, for example, with a chemical absorption solution.

As an example, alkaline media are suitable for the removal of sulphur dioxide.

As a result of this selective chemical toxic substance removal, a differential measurement or a differential signal occurs between sensor 1 and sensor 2, resulting from the selective removal fraction.

Thus, this indirectly permits the provision of a selective measured value between sensor 1 and sensor 2.

Selective removal can also be effected, for example, by means of a molecular sieve.

Without deviating from the basic concept, many selective removal methods are possible between sensor 1 and sensor 2 or by the use of several sensors connected one in the other so as to remove specific toxic substances selectively, thereby making different signals identifiable which can then be associated with the individual components of the toxic substance.

It is known that semiconductor gas sensors can be provided with positive ventilation, in which connection the air masses can be caused to oscillate in front of the surface of the sensor, this being done by means of an oscillator pump. These pumps are then subject to normal wear and tear.

In order to minimize this wear, the present invention provides that the DC armature of the oscillating magnet be floating, this being done between a tension and a compression spring.

The advantage of this can be seen particularly in that very economical DC plunge magnet armtures can be used. By this means it is possible to generate an oscillating movement without mechanical impact limits, by means of the floating suspension between tension and compression springs, and this in turn leads to reduced wear during operation.

BRIEF DESCRIPTION OF THE DRAWINGS

The present invention will be described in greater detail below, on the basis of the drawing appended hereto. In the drawing.

SPECIFIC DESCRIPTION

Figure 1:
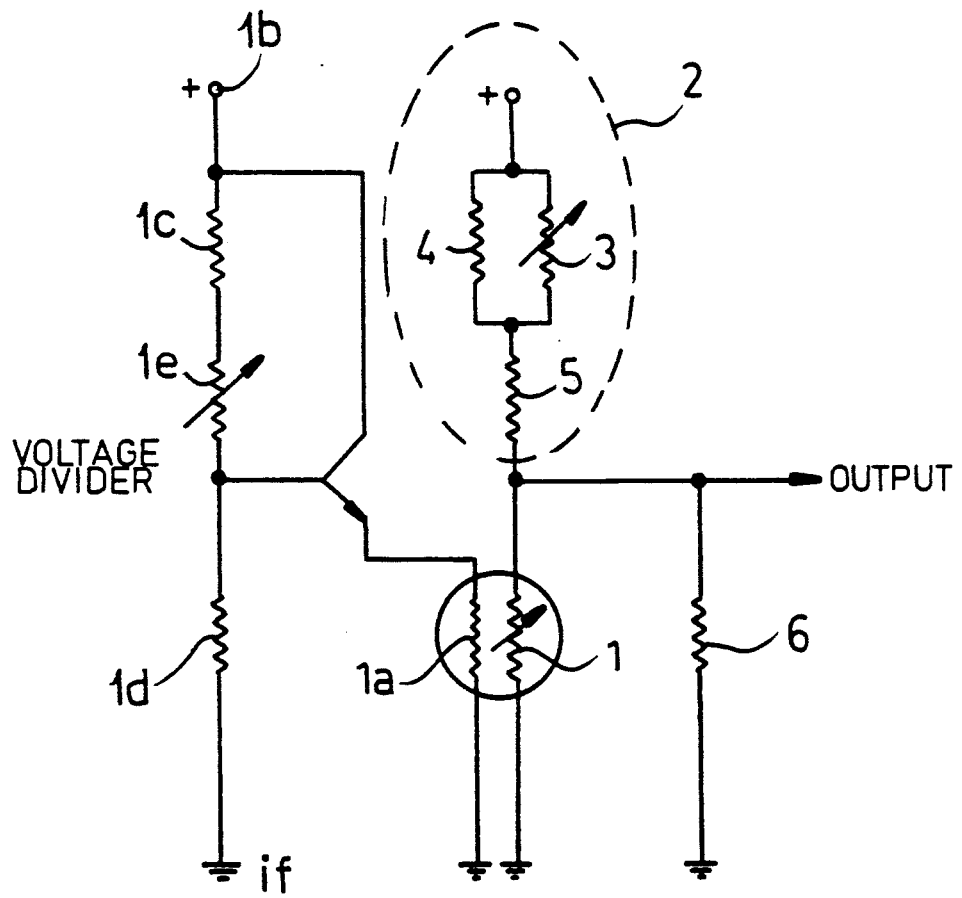
FIG. 1 is a circuit diagram for compensation of the effects caused by temperature and air humidity.

In FIG. 1, the sensor 1 is connected in series with an external resistance and has the usual heater 1a energized through a transistor circuit including a source 1b, fixed bias resistors 1c, 1d, a variable resistor 1e and a ground 1f. The transistor is shown at 1g.

The external resistor 2 consists of a temperature dependent resistance 3 with a negative temperature coefficient as well as at 4 a paralle linearizing resistance and a series connecting limiting resistance 5. A linearizing resistance 6 is incorporated in parallel to the sensor in order to linearize the non-linear characteristic curve of the sensor.

Modulation of the heating voltage is carried out as voltage modulation in which a positive temperature coefficient resistance is installed in the positive branch. It is also possible to provide a negative temperature coefficient resistance in the negative branch of the voltage divider between the source 1b and the ground 1f.

Figure 2:
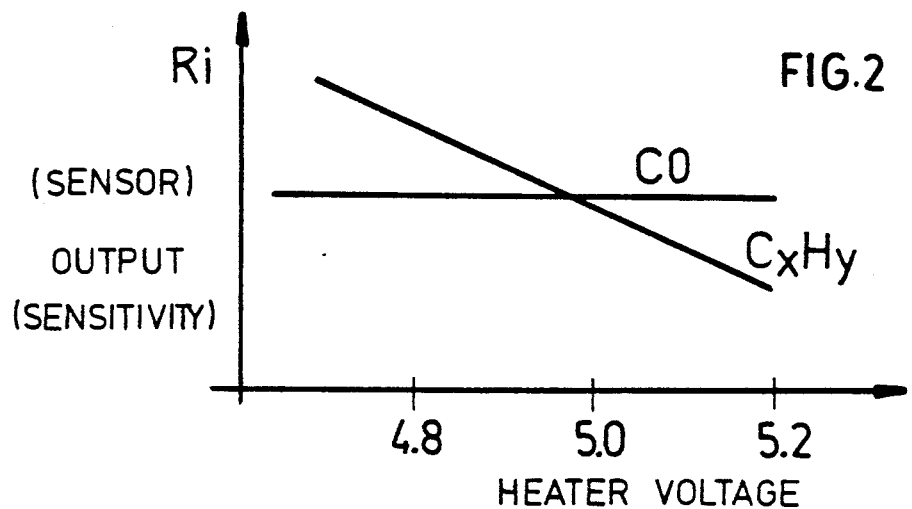
FIGS. 2-4 are the characteristic curves of the sensors that are used.

The characteristic curve field of FIG. 2 shows the dependency of sensor sensitivity on heating voltage for various gases.

Figure 3:
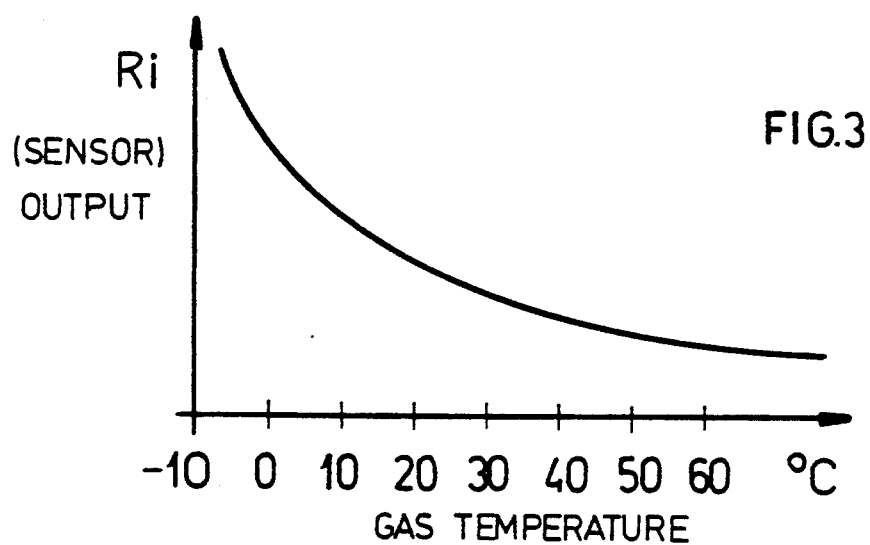

In the characteristic curve field as of FIG. 3 the shape of the uncorrected sensor sensitivity curve for complex gas mixtures such as automobile exhausts is shown.

Figure 4:
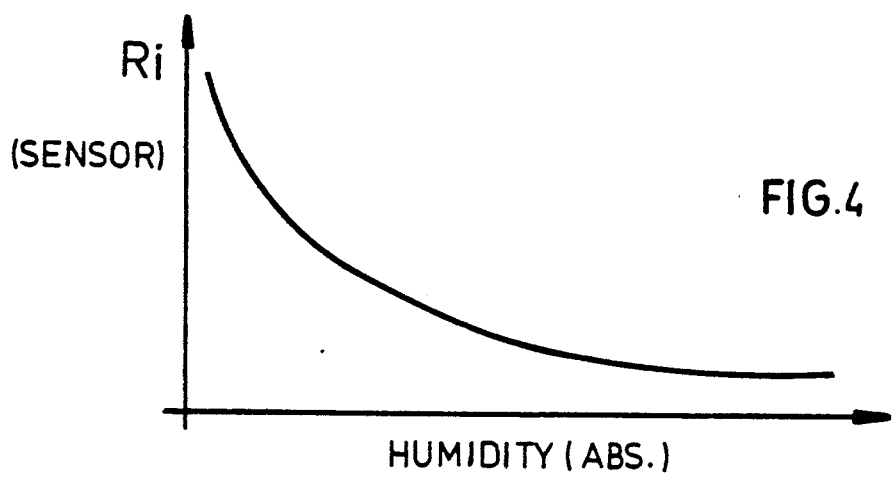

FIG. 4 shows the dependency of the internal sensor resistance at a carbon monoxide concentration of 20 ppm as a function of absolute air humidity.

Figure 5:
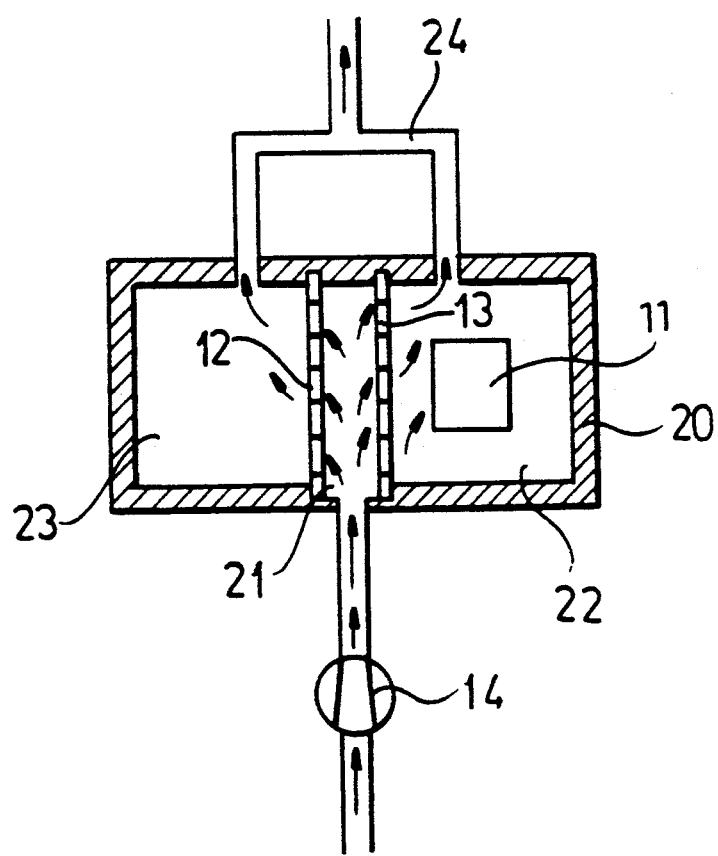
FIG. 5 is a sectional view of a sensor.

In FIG. 5 the semiconductor gas sensor 11 is located in a housing 20 outside the passage 21 delimited by a foil 12, which preferably permits the passage of non-injurious gases. The foil 13 closing the sensor compartment 22 permits the passage of all gases. The gas pump 14 feeds passage 21. Thus a portion of the nontoxic components of the gas pass through the foil 12 into the compartment 23 so that the concentration of the toxic component in the gases passing through foil 13 into the detector compartment is increased. The gases are carried off through duct 24.

The stabilization of semiconductor gas sensors takes place in this embodiment in that the polluted air that is to be picked up is brought to a greater concentration of toxic substances by means of gas-permeable foils with which some clean air is separated out by means of membrane technology.

We claim:

1. An apparatus for indicating the presence of carbon monoxide in an air stream supplied to a personnel-occupied space, comprising:
   a resistive sensor constructed so as to detect carbon monoxide and across which an output is tapped;
   means for passing at least a portion of said air stream into contact with said sensor whereby said output across said sensor signals the detection of said carbon monoxide;
   a resistive heater juxtaposed with said sensor;
   a transistor circuit including a transistor connected to said heater and provided with a first voltage divider for controlling a voltage applied to said heater, said first voltage divider being provided with a first temperature-compensating component connected to a voltage source to control the voltage applied to said heater responsive to temperature of said air stream to provide a substantially constant heat output at said heater; and
   an external resistance connected in series with said sensor to form a second voltage divider connected to said source and including a second temperature-compensating component, said first and second components being matched so that said first and second voltage dividers compensate each other with respect to a temperature response of the output across said sensor proportional with concentration of said carbon monoxide to be measured to eliminate a temperature effect upon the detection of said carbon monoxide.

2. An apparatus for indicating a presence of carbon monoxide to be measured of an air stream supplied to a personnel-occupied space, comprising:

means for dividing the air stream into two portions by passing said air stream through a barrier for the carbon monoxide in the air stream thereby separating a first portion of the air stream comprising said carbon monoxide to be measured from a second portion containing less of said carbon monoxide;

means for passing said first portion with said carbon monoxide to be measured of said air stream into contact with an electrical sensor for said carbon monoxide to be measured and detecting an electrical output across said sensor signalling the detection of said carbon monoxide;

an electrical heater juxtaposed with said sensor and provided with means for controlling a voltage applied to said heater in response to temperature of said air stream to provide a substantially constant heat output at said heater, said means for control comprising a first voltage divider in electrical circuit with said heater which is provided with a first temperature-compensating component connected to a voltage source; and means electrically connecting said sensor in electrical series with an external electrical resistance to form a second voltage divider connected to a voltage source, including a second temperature-compensating component, and independent from said first voltage divider, said temperature-compensating components being matched so that said voltage dividers compensate each other with respect to a temperature response of the output across said sensor proportional with concentration of said carbon monoxide to be measured to eliminate a temperature effect upon the detection of said carbon monoxide.

* * * * *